United States Patent [19]

Bittle et al.

[11] Patent Number: 4,544,500

[45] Date of Patent: Oct. 1, 1985

[54] SYNTHETIC FOOT AND MOUTH DISEASE ANTIGEN

[75] Inventors: James L. Bittle, San Diego; Richard A. Lerner, La Jolla, both of Calif.

[73] Assignee: Scripps Clinic and Research Foundation, La Jolla, Calif.

[21] Appl. No.: 682,819

[22] Filed: Dec. 18, 1984

Related U.S. Application Data

[63] Continuation of Ser. No. 368,308, Apr. 14, 1982, abandoned.

[51] Int. Cl.[4] .................. C07C 103/52; C07G 7/00
[52] U.S. Cl. ..................... 260/112.5 R; 260/112 R
[58] Field of Search ................. 260/112.5 R, 112 R

[56] References Cited

FOREIGN PATENT DOCUMENTS 2079288  1/1982  United Kingdom .

OTHER PUBLICATIONS

Sutcliffe, et al., Nature, vol. 287, (1980), 801–805.
Walter, et al., Proc. Nat'l. Acad. Sci., 77, (1980) 5197–5200.
The EMBO Journal, vol. 1, No. 7, 869–874 (1982).

Primary Examiner—Delbert R. Phillips
Attorney, Agent, or Firm—Dressler, Goldsmith, Shore, Sutker & Milnamow, Ltd.

[57] ABSTRACT

Synthetic antigens in which the principal antigenicity derives from synthetic peptide corresponding to the 130–160 region of the foot-and-mouth disease virus are described.

4 Claims, No Drawings

SYNTHETIC FOOT AND MOUTH DISEASE ANTIGEN

This application is a continuation of application Ser. No. 368,308 filed Apr. 14, 1982, now abandoned.

TECHNICAL FIELD

The present invention relates to vaccines and antigens for infectious diseases and, more specifically, to antigens useful in the diagnosis and treatment of foot-and-mouth disease.

BACKGROUND

Foot-and-mouth disease is a highly contagious disease of great economic importance, afflicting primarily cloven-hoofed animals. The mortality directly attributable to foot-and-mouth disease is comparatively low, generally, but in young animals the mortality can be quite high. Of greater economic importance, the disease is so debilitating that infected animals cannot economically be raised and fed. The only recognized effective procedure for eliminating the infection once it has been discovered is to destroy all infected animals, disinfect all premises which have been occupied by the animals, and decompose the carcasses in quicklime. Since the infection spreads extremely rapidly, the economic foundation of entire communities or regions can be destroyed by one major outbreak of foot-and-mouth disease.

Vaccines have been produced which immunize against foot-and-mouth disease, primarily, by inactivation or attenuation of virus. Such vaccines have been found to be effective in some measure, but outbreaks of foot-and-mouth disease have been linked to vaccines in which the virus was incompletely inactivated or insufficiently attenuated. Infections have also been traced to the escape of virus from facilities devoted to research on foot-and-mouth disease or to production of foot-and-mouth disease vaccines.

Foot-and-mouth disease (FMD) is caused by a picornavirus of the family Aphthovirus. There are several viral serotypes of foot-and-mouth virus (FMDV), the most common of which are identified by the serotype designations A, O and C, and less common identified as SAT-1, SAT-2, SAT-3 and ASIA-1.

FMDV has been described in some detail; see, for example, (H. L. Backrach, in *Beltsville Symposium on Agricultural Research*, J. A. Romberger, Ed. (Allanheld, Montclair, N.J. 1977), pp. 3-32; Annual Reviews of Microbiology, 22, 201 (1968).) The molecular biology of these viruses have been described, R. R. Rueckert, in *Molecular Biology of Picornavizuses*, R. Perez-Bercoff, Ed. (Plenum, New York, 1979), p. 113. The virus has a molecular size of about $7 \times 10^6$ daltons and contains a plus-stranded RNA genome of approximately 8,000 nucleotides. Picornavirus proteins have been synthesized in infected cells as a precursor of a protein that is subsequently processed by cellular and virus-coded proteases into four major capsid proteins ($VP_1$, $VP_2$, $VP_3$, and $VP_4$) and numerous non-capsid proteins. The $VP_3$ protein when used to inoculate swine ellicited a neutralizing anti-body response and protected both swine and cattle from infection. (J. Laporte, et al., C.R. Acad. Sci. 276, 3399 (1973); H. L. Backrach, et al., J. Immunol. 115, 1636 (1975); H. L. Backrach, et al., Vet. Microbiol.) Based upon this information, Dennis G. Kleid, et al. Science, Vol. 214, 4 Dec. 1981, 1125–1129, were able to produce a cloned viral protein vaccine for foot-and-mouth disease which gave anitbody responses in cattle and swine. Recombinant DNA molecules and processes for producing peptides with the specificity of foot-and-mouth disease viral antigens is described in UK patent application GB No. 2,079,288A, 20 Jan. 1982. K. Strohmaier, et al., Proc. 5th Int. Congress Virology, Strasbourg, 1981, have suggested that regions of the VP protein sequence between positions 146 and 155 and positions 200–213 would be effective in inducing antibodies to the foot-and-mouth disease virus; however, no affirmative demonstration of the use of these regions as antigens has been reported. This $VP_1$ sequence corresponds to the $VP_3$ sequence described earlier in the United States; see explanation by Meloen, A. H., *J.Gen.Virol.* (1979) 45, 761–763.

In the past antigens have been obtained in several fashions, including derivation from natural materials, coupling of a hapten to a carrier, and by recombinant DNA technology. Sela, et al. (*Proc. Nat. Acad. Sci.*, U.S.A., Vol. 68, No. 7, pp. 1450–1455, July 1971; *Science*, Vol. 166, pp. 1365–1374, December 1969; *Adv. Immun.*, Vol. 5, pp. 29–129, 1966) have also described certain synthetic antigens.

Antigens derived from natural materials are the countless number of known antigens which occur naturally, such as blood group antigens, HLA antigens, differentiation antigens, viral and bacterial antigens, and the like. Considerable effort has been expended over the last century in identifying and studying these antigens.

Certain "synthetic" antigens have been prepared by coupling small molecules to carriers such as, for example, bovine serum albumin, thus producing antigens which will cause production of antibody to the coupled small molecule. The carrier molecule is necessary because the small molecule itself would not be "recognized" by the immune system of the animal into which it was injected. This technique has also been employed in isolated instances to prepare antigens by coupling peptide fragments of known proteins to carriers, as described in the above-referenced Sela et al. articles.

While this hapten-carrier technique has served the research community well in its investigations of the nature of the immune response, it has not been of significant use to produce antigens which would play a role in diagnostic or therapeutic modalities. The reasons for this deficiency are several.

First, to choose and construct a useful antigenic determinant from a pathogen by this technique, one must determine the entire protein sequence of the pathogen to have a reasonable change of success. Because of the difficulty of this task it has rarely, if ever, been done.

Classically, vaccines are manufactured by introducing killed or attenuated organisms into the host along with suitable adjuvents to initiate the normal immune response to the organisms while, desirably, avoiding the pathogenic effects of the organism in the host. The approach suffers from the well known limitations in that it is rarely possible to avoid the pathogenic response because of the complexity of the vaccine which includes not only the antigenic determinant of interest but many related and unrelated deleterious materials, any number of which may, in some or all individuals, induce an undesirable reaction in the host. For example, vaccines produced in the classical way may include competing antigens which are detrimental to the desired immune response, antigens which include unrelated immune responses, nucleic acids from the organism or culture, endotoxins and constituents of unknown composition and source. These vaccines, generated from complex materials, inherently have a relatively high probability of inducing competing responses even from the antigen of interest.

Recombinant DNA technology has opened new approaches to vaccine technology which does have the advantage that the manufacture begins with a monospecific gene; however, much of this advantage is lost in actual production of antigen in *E. coli,* or other organisms. In this procedure, the gene material is introduced into a plasmid which is then introduced into *E. coli* which produces the desired protein, along with other products of the metabolism, all in mixture with the nutrient. This approach is complicated by the uncertainty whether the desired protein will be expressed in the transformed *E. coli.* Further, even though the desired protein may be produced, there is uncertainty as to whether or not it can be harvested or whether it will be destroyed in the process of *E. coli* growth. It is well known, for example, that foreign or altered proteins are digested by *E. coli.* Even if the protein is present in sufficient quantities to be of interest, it must still be separated from all of the other products of the *E. coli* metabolism, including such deleterious substances as undesired proteins, endotoxins, nucleic acids, genes and unknown or unpredictable substances. Finally, even if it were possible, or becomes possible through advanced, though necessarily very expensive, techniques, to separate the desired protein from all other products of the *E. coli* metabolism, the vaccine still comprises an entire protein which may include undesirable antigenic determinants, some of which are known to initiate very serious responses. Indeed, it is known that certain proteins which could otherwise be considered as vaccines include an antigenic determinant which induce such serious cross reference or side reactions as to prevent the use of the material as a vaccine.

It is also possible, using hybridoma technology, to produce antibodies to viral gene products. Basically, hybridoma technology allows one to begin with a complex mixture of antigens and to produce monospecific antibodies later in the process.

In contrast, the present invention is the reverse process, in that we start with the ultimate in high purity antigenic determinant and thus avoid the necessity for purification of the desired antigenic product.

Hybridoma antibodies are known to be of low avidity and low binding constant, and therefore, have limited value.

Ultimately, in hybridoma technology, one must rely on the production of the antibody by cells which are malignant, with all of the attendant concerns regarding separation techniques, purity and safety.

Hybridoma production relies upon tissue culture or introduction into mice, with the obvious result that production is costly and there is inherent variability from lot to lot.

In addition, it is difficult to make a hybrid to molecules which comprise only a small percentage of the complex mixture one must start with.

Previous studies by Arnon et al. (1971, *Proc. Nat. Acad. Sci.* 68:1450), Atassi (1975, *Immunochemistry* 12:423) and Vyas et al. (1972 *Science* 178:1300) have been interpreted by these authors to indicate that short linear amino acid sequences are, in general, unlikely to elicit antibodies reactive with the native protein structure. It was thought that for most regions of most molecules, antigenic determinants resulted from amino acid residues well separated in the linear sequence but conformation of the peptides used to elicit antibodies was thought to be critical in most cases, even for those antigens involving amino acids close together in a sequence. Lerner, et al., *Cell* 23:109–110, 1981; *Nature* 287:801–805 (1980), discovered that antibodies to linear peptides react with native molecules. Elaborate biosyntheses thus became unnecessary, uneconomical and obsolete.

Notwithstanding the availability of inactivated or attenuated virus vaccines against foot-and-mouth disease, there has remained a very great economic and practical demand, and great theoretical interest in the development of a vaccine against foot-and-mouth disease which would be free of the risks which have heretofore attended the manufacture and handling of the FMDV which causes the disease. The availability of cloned viral proteins may well be a very significant step forward from the older and very risky approaches. But the cloned viral protein vaccine approach also carries with it a number of inherent disadvantages, limitations and risks. Variations in the biosynthesis system itself may cause variation in expression of proteins, thus affecting purity, yields, potency, etc. of antigens. The possibility of finding live or active organisms in the resulting product is always a potential risk. in addition, the presence of other proteins, and difficult and inefficient separations, suggest the likelihood that vaccines produced through the cloned viral protein route will not be monospecific. Indeed, Kleid, et al. suggested that there was evidence that the antibodies to $VP_3$ elicit antibodies to several different antigenic sites. Thus, purity, potency, and safety are major concerns with products derived from this technology.

Notwithstanding that the general concept of preparing synthetic antigens, starting either from a known peptide sequence or from a genome have been described, and notwithstanding that the synthesis of peptides of suitable length for use in antigenic materials is now quite well known, there remains a very large area of antigen-antibody technology which continues to defy predictability. While there are some guidelines and some suggestions as to possible antigenic sequences, the field remains largely a matter of speculation, and of trial and error. Even with the recognition that a long sequence may contain antigenically active constituents, there remains a great deal of uncertainty and speculation as to whether all or only part of the sequence is required for antigenicity, and whether or not a smaller portion of the sequence would be of greater or lesser antigenicity.

STATEMENT OF THE INVENTION

The present invention comprises the discovery that a particular, comparatively short, peptide sequence is, most unexpectably and most surprisingly, extremely active antigenically, and that synthetic antigens in which the peptide sequences described hereinafter are monospecific to the specific serotypes of foot-and-mouth disease virus.

In particular, it has been discovered, according to the present invention, that the peptide corresponding to positions 130–160, and positions 141–160 especially, of FMDV $VP_1$ protein have much higher antigenic efficacy and activity that ever had been suggested or predicted from earlier studies.

Exemplary of the peptides which are encompassed in the present invention are the 130–160 region of Tubingen type O and type A FMDV proteins, and the corresponding regions of type C, SAT-1, SAT-2, SAT-3 and ASIA-1, two examples of which are:

EXAMPLE 1

TYR ASN GLY GLU CYS ARG TYR ASN ARG ASN ALA VAL PRO ASN LEU ARG
(130)                                    (140)

GLY ASP LEU GLN VAL LEU ALA GLN LYS VAL ALA ARG THR LEU PRO
(150)                                    (160)

EXAMPLE 2

TYR ASN GLY THR ASN LYS TYR SER ALA SER GLY SER GLY VAL ARG GLY ASP
(130)                                    (140)

PHE GLY SER LEU ALA PRO ARG VAL ALA ARG GLN LEU PRO ALA
(150)                                    (160)

It has also been established that the 141 to 160 region is uniquely and highly unexpectedly antigenically active and potent, as discussed in greater detail herein.

Peptides having a sequence of approximately twenty amino acids, within the 130 to 160 region, in the 141–160 region in particular, to which a CYS or other amino acid may be added to permit attachment to a carrier, e.g. KLH, if a carrier is to be used, embody the invention, as do the above with variations in peptide fragment length or substitutions as to individual amino acids which do not destroy or substantially alter the unique and potent antigenicity exhibited by the FMDV mono-specific synthetic antigenic determinant peptides of this invention.

These sequences, separated from other antigenically active or antigenically masking sequences, constitute the invention in one form. Antigens comprising more than one of the foregoing antigenically active sequences, separate from antigenically interfering or masking sequences, chemically associated or mixed with each other constitute another form of the invention. Antigens comprising a carrier to which one or more of the foregoing antigenically active amino acid sequences is attached constitutes another embodiment of the invention. The invention, of course, also embodies the vaccine with or without adjuvents.

In considering the present invention it is important to recognize the following definition of the antigenically active amino acid sequences which are considered as one embodiment of the invention. The sequence, for example, Val Pro Asn Leu Arg Gly Asp Leu Gln Val Leu Ala Gln Lys Val Ala Arg Thr Leu Pro when separated from other peptides, gene fragments, amino acids and amino acid sequences which tend to mask or to interfere with or to cross-react or complicate the antigenic effectiveness of the subject peptide is considered to be the subject invention. Thus, while one may find the specified sequence as part of a large protein or a large peptide, such would not constitute the invention because a large protein or a large peptide would not possess the activity, the unusually and unexpectedly high level of substantially monospecific antigenic activity, possessed by an amino acid sequences, etc.

The term, "FMDV mono-specific synthetic antigenic determinant peptide" means the particular peptide specified as described above resulting from synthesis which eliminates the possibility of fragments of genes, proteins or peptides, or any amino acid compound orginating directly or indirectly from FMDV and free of peptide or amino acid sequences which would interfere with or alter the monospecific antigenic activity of the specified peptide in inducing antibody production to FMDV in animals.

As a vaccine, the present invention comprises an antigen which may, alone, serve as the vaccine. The vaccine may include a carrier, which may be of any of numerous recognized carriers, to which a FMDV monospecific synthetic antigenic determinant peptide is bound. In both instances, the peptide functions as the specific antigenic determinant. When the antigen is introduced into the desired host, it initiates the production of antibodies in the host to the aforesaid antigenic determinant portion and to FMDV. The invention also contemplates antigens in which all or part of the entire carrier is antigenic. Thus, a separate carrier portion may or may not be used.

The synthetic antigen formed by coupling the FMDV mono-specific synthetic antigenic determinant peptide to an antigen carrier as well as the methods of preparing such synthetic antigens are specific aspects of the present invention.

In general, the synthetic antigen may be formed by the steps of preparing the FMDV mono-specific synthetic antigenic determinant peptide, which immunologically duplicates antigenic determinants of FMDV, and coupling the synthetic determinant to a pharmaceutically acceptable carrier.

As a method of manufacturing vaccines, the method comprises synthesizing FMDV mono-specific synthetic antigenic determinant peptide which antigenically is the duplicate or substantial duplicate of specified determinant portion of the protein. The synthetic peptide may be, but need not always be, attached to a carrier, to result in an antigen in which the antigenicity is that of the FMDV mono-specific synthetic antigenic determinant peptide and which, when introduced into a host, initiates production of antibodies to FMD virus.

As a method of manufacturing antibodies, the vaccine as described above is injected into a host and antibodies to the protein antigen are harvested from host fluids for use in conventional diagnostic procedures to detect the presence of the protein antibody or as therapeutic agents for passive immunoprophylaxis.

It will be understood that while there are many procedural steps utilizing many materials in the manufacture of the vaccines and antibody preparations of this invention, as discussed in detail hereinafter, the invention is not limited to the utilization of any particular steps or reagents or conditions, but rather the invention is conceptually as stated above and as defined with particularity in the claims appended hereto.

Peptides were synthesized using known procedures. (See, e.g., Marglin, A. and Merrifield, R. B., Ann.Rev. Biochem. 39, 841-866 (1970).) The peptides were coupled to a protein carrier KLH through the cysteine which was synthesized to the peptide by using N-maleimidobenzoyl-N-hydroxy succinimid ester (MBS), as described by Lieu et al, Biochemistry 18, 690–697 (1979). Assay was by ELISA.

Responses to various peptide regions of the VP$_1$ protein are given in Table 1. These data summarize antibody response in rabbits, using conventional protocols. (See, e.g. for details of exemplary protocols, Lerner et al patent application Ser. No. 248,059 filed Mar. 27, 1981, and Bittle J. L., Houghten, R. A., Alexander, H., Shinnick, T. M., Sutcliffe, J. G., Lerner, R. A., Rowlands, D. J. and Brown, F., "Protection Against Foot-and-Mouth Disease by Immunization With a Chemically Synthesized Peptide Predicted From the Viral Nucleotide Sequence," Nature 298, 30–33 (1982).)

TABLE 1

ANTIBODY RESPONSE TO DIFFERENT PEPTIDES

| Peptide | Neutralization Index (log) |
|---|---|
| 9–24 | ≦0.3 |
| 9–24 | ≦0.3 |
| 17–32 | ≦0.5 |
| 17–32 | ≦0.9 |
| 25–41 | ≦0.5 |
| 25"41 | ≦0.9 |
| 1–41 | ≦0.9 |
| 1–41 | ≦0.7 |
| 141–160 | ≧3.9 |
| 141–160 | 3.7 |
| 151–160 | 2.9 |
| 151–160 | 1.1 |
| 200–213 | 3.5 |
| 200–213 | 3.1 |

It was established that a single inoculation of the antigens was effective in producing neutralizing antibodies in animals and in protecting them against challenge. Table 2 summarizes these results, on guinea pigs, carried out using standard protocol (see Lerner et al patent application and Bittle et al publication, supra). Table 2 shows the efficacy of the antigens and, also, shows the markedly surprising antigenicity of the 141–160 region of the VP$_1$ protein. A neutralizing index of c. 1.5 or greater indicates that the animal was protected against the virus.

TABLE 3

PROTECTION OF ANIMAL AGAINST CHALLENGE WITH FOOT-AND-MOUTH DISEASE VIRUS BY INNOCULATION SYNTHETIC PEPTIDE 141–160

| Antigen | Dose | Adjuvant | Neutralization Index (log) | Protection No. Protected/ No. Challenged |
|---|---|---|---|---|
| P141–160 | 20 μg | Al(OH)$_3$ | 2.1 | 3/4 |
| | 200 μg | Al(OH)$_3$ | 2.7 | 3/3 |
| | 20 μg | Freund's | 2.1 | 1/4 |
| | 200 μg | Freund's | 3.3 | 4/4 |
| P200–213 | 20 μg | Al(OH)$_3$ | 1.1 | 1/3 |
| | 200 μg | Al(OH)$_3$ | 0.7 | 2/4 |
| | 20 μg | Freund's | 1.1 | 0/4 |
| | 200 μg | Freund's | 0.5 | 0/4 |

In a general sense, then, one aspect of the invention is a process for producing FMDV vaccines which have all of the immunizing effect of prior art vaccines but which are totally free of competing or cross referencing immunological side effects.

The method of the invention may be used in the preparation of diagnostic tests, such as immunoassays, in which it is necessary to have antibodies to the organism to be detected or a synthetic antigen mimicking a determinant on the organism to be detected. Such diagnostic techniques include, for example, enzyme immune assay, radioimmune assay, fluorescence immune assay, and other techniques in which either the antibody or the antigen is labelled with some detectable tag.

For example, using the double antibody technique outlined by Voller, et al., "Enzyme Immune Assays in Diagnostic, Medicine", *Bulletin of the World Health Organization*, Volume 53, pp. 55–65 (1976), an ELISA Test may be used in the preparation of diagnostic tests.

Methods and materials unique to this invention are described with the particular procedure under consideration. In general, however, specific laboratory techniques, methods and materials are those used in molecular biology and biochemistry generally.

Particular reference is made to METHODS IN ENZYMOLOGY, Colowick, S. P. and Kaplan, N. O., Editors, Academic Press, New York; METHODS IN IMMUNOLOGY AND IMMUNOCHEMISTRY, Academic Press, HANDBOOK OF BIOCHEMISTRY AND MOLECULAR BIOLOGY, Chemical Rubber Publishing Company, and CELL BIOLOGY: A COMPREHENSIVE TREATISE, Goldstein and Prescott, Academic Press, N.Y., N.Y. for a description of a reference to the general materials and techniques of interest.

The following references disclose particular steps in the prior art and techniques and the current state of the art.

REFERENCES

1. Baltimore, D., Cold Spring Harbor Symp., *Quant. Biol.* 39, 1187–1200 (1974).
2. Oskarsson, M. K., Elder, J. H., Gautsch, J. W., Lerner, R. A. and Vande Woude, G. F., *Proc. Natl. Acad. Sci.*, U.S.A. 75, 4694–4698 (1978).
3. Gautsch, J. W., Elder, J. H., Schindler, J., Jensen, F. C., and Lerner, R. A., *Proc. Natl. Acad. Sci.*, U.S.A. 75, 4170–4174 (1978).
4. Jamjoon, G. A., Naso, R. B. and Arlinghaus, R. B., *Virol.* 78, 11–34 (1977).
5. Famulari, N. C., Buchhagen, D. L., Klenk, H. D., and Fleissner, E., *J. Virol.* 20, 501–508 (1976).
6. Witte, O. N., Tsukamoto-Adey, A. and Weissman, L. L., *Virol.* 76, 539–553 (1977).
7. Fan, H. and Verma, I. M., *J. Virol.* 26, 468–478 (1978).
8. Sutcliffe, J. G., Shinnick, T. M., Lerner, R. A., Johnson, P. and Verma, I. M., Cold Spring Harbor Symp. *Quant. Biol.* 44, in press (1979).
9. Sutcliffe, J. G., Shinnick, T. M., Verma, I. M. and Lerner, R. A., *Proc. Natl. Acad. Sci.*, U.S.A., in press (1980).
10. Marglin, A. and Merrifield, R. B., *Ann. Rev. Biochem.* 39, 841–866 (1970).
11. Pederson, F. S. and Haseltine, W. A., *J. Virol.* 33, 349–365 (1980).
12. *Atlas of Protein Sequence and Structure*, Vol. 5, Sup. 3, M. O. Dayhoff, ed., Natl. Biomed. Res. Found., pub. Washington, D.C. (1978).
13. Dayhoff, M. O., Schwartz, R. M. and Orcutt, B. C., pp. 352, op. cit.
14. Fisher, R. A., *The Genetical Theory of Natural Selection*, Clarendon Press, Oxfore (1930).
15. Elder, J. H., Gautsch, J. W., Jensen, F. C., Lerner, R. A., Harley, J. W. and Rowe, W. P., *Proc. Natl. Acad. Sci.*, U.S.A. 74, 4676–4680 (1977).

16. Lerner, R. A., Jensen, F. C., Kennel, S. J., Dixon, F. J., Roches, G. D. and Francke, U., *Proc. Nat. Acad. Sci., U.S.A.* 69, 2965–2969 (1972).
17. Niman, H. L. and Elder, J. H., *Proc. Nat. Acad. Sci., U.S.A.*, in press (1980).
18. Edwards S. A. and Fan, H., *J. Virol,* 30, 551–563 (1979).
19. Kitagawa, T. and Ailawa, T., *J. Biochem.* (Tokyo) 79, 233 (1976).
20. Liu, F., Zinnecker, M., Hamaoka, T. and Katz, D. H. *Biochem.* 18, 690 (1979).
21. Katz, David H., U.S. Pat. No. 4,191,668, Mar. 4, 1980.
22. *J. Exp. Med.*, 134: 201–203 (1971).
23. *J. Exp. Med.*, 136: 426–438, 1404–1429 (1972).
24. *J. Exp. Med.*, 138: 312–317 (1973).
25. *J. Exp. Med.*, 139: 1446–1463 (1974).
26. *Proc. Natl. Acad. Sci.*, U.S.A., 71: 3111–3114.
27. *Proc. Natl. Acad. Sci.*, U.S.A., 73: 2091–2095 (1976).
28. *J. Immunol.* 144: 872–876 (1975).
29. *J. Immunol.* 120: 1824–1827 (1978).
30. *J. Exp. Med.*, 139: 1464–1472 (1974).
31. Humphrey, J. H. and White, R. G., *Immunology for Students of Medicine,* Blackwell, Oxford (1970).
32. Katz, David H. and Benacerraf, Baruj, *Immunological Tolerance, Mechanisms and Potential Therapeutic Applications,* Academic Press (1974).
33. *Newsweek,* Mar. 17, 1980, pp. 62–71.
34. *Chemical & Engineering News,* June 23, 1980, p. 10.
35. Milstein, C., *Differentiation* 13: 55 (1979).
36. Howard, J. C., Butcher, G. W., Galfre', G., Milstein, G. and Milstein, C. P., *Immunol. Rev.* 47: 139 (1979).
37. Hammerling, G. J., Hammerling, U., and Lemke, H., *Immunogenetics* 8: 433 (1978).
38. Shulman, M., Wilde, C. D., and Köhler, G., *Nature* 276: 269 (1978).
39. Köhler, G. and Milstein, G., *Nature* 256: 495 (1975).
40. Ledbetter, J. A. and Herzenberg, L. A., *Immunol. Rev.* 47: 63 (1979).
41. Gefter, M. L., Margulies, D. H. and Scharff, M. D., *Somatic Cell Genetics* 3: 231 (1977).
42. Köhler, G. and Milstein, C., *Eur. J. Immunol.* 6: 511 (1976).
43. *J. Biol. Chem.*, 241: 2491–2495 (1966).
44. *J. Biol. Chem.*, 242: 555–557 (1967).
45. Koprowski, Hilary et al., U.S. Pat. No. 4,196,265, April 1980.
46. *Science* 209, No. 4463, pp. 1319–1438 (September 1980—entire number).
47. Davis, B. D., Dulbecco, R. Eisen, H. N., Ginsbert, H. S., Wood, W. B. Jr., and McCarty, M., *Microbiology,* Harper & Row, Hagerstown, Md., 1973.
48. Morgan, J. and Whelan, W. J., *Recombinant DNA And Genetic Experimentation,* Pergamon Press, New York, 1979.
49. Goldstein, L. and Prescott, D. M., *Cell Biology, A Comprehensive Treatise,* Vols. 1, 2 & 3, Academic Press, San Francisco.
50. Scott, W. A. and Werner, R., *Molecular Cloning of Recombinant DNA,* Academic Press, New York, 1977.
51. Wu, Ray (Ed.), Colowick, Sidney P., and Kaplan, Nathan O., *Methods in Enzymology,* generally and Vol. 68, "Recombinant DNA" in particular, Academic Press, New York.
52. Cooper, Terrance G., *The Tools of Biochemistry,* John Wiley & Sons, New York, 1977.
53. Sela, Michael, *Science* 166: 1365–1374 (1969).
54. Arnon, R., Elchanan, M., Sela, M. and Anfinsen, C. B., *Proc. Natl. Acad. Sci.* U.S.A., 68: 1450 (1971).
55. Sela, M., *Adv. Immun.* 5: 29–129 (1966).
56. Sela, M., Arnon, R., and Chaitchik, S., U.S. Pat. No. 4,075,194, Feb. 21, 1978.
57. Cohen, S. N., and Boyer, H. W., U.S. Pat. No. 4,237,224, Dec. 2, 1980.
58. Lerner, R. A., Sutcliffe, J. G. and Shinnick, T. M. (1981) *Cell* 23: 109–110.
59. Wilson, I. A., Skehel, J. J. and Wiley, D. C. (1981), *Nature* 289: 366–373.
60. Sutcliffe, J. G., Shinnick, T. M., Green, N., Liu, F-T, Niman, H. L., and Lerner, R. A. (1980), *Nature* 287: 801–805.
61. Kleid, D. G., Yansura, D., Small, B., Dowbenko, D., Moore, D. M., Grubman, M. J., McKercher, P. D., Morgan, D. O., Robertson, B. H., Bachrach, H. L., *Science* 214: 1125–1129 (1981).
62. CELL BIOLOGY, A COMPREHENSIVE TREATISE, Goldstein, L., and Prescott, D. M., Eds., Academic Press, N.Y., 1977 et. seq.
63. MOLECULAR BIOLOGY OF THE GENE, 3rd Ed., Watson, J. D., W. A. Benjamin, Inc., Menlo Park, CA. 1977.
64. *Scientific American,* "Recombinant DNA" W. H. Freeman and Company, San Francisco 1978.
65. Nofschneider, P., Heinz, S., Kupper, H. A., Keller, W., UK patent application No. GB 2 079 288 A, published 20 Jan. 1982.
66. Kupper, H., Keller, W., Kunz, C., Forss, S., Scholler, H., Franze, R., Strohmair, K., Marquardt, O., Zaslovsky, V. G., and Hofschneider, P. H., "Cloning of cDNA of major antigen of foot and mouth disease virus and expression in *E. Coli,*" *Nature* 289: 555–559 (1981).
67. Walter, G., Scheidtmann, K., Carbone, A., Laudano, A. P., Doolittle, R. F., *Proc. Natl. Acad. Sci. USA* 77: 5197–5200 (1980).
68. Fracastorius, H. DeContagione et Contagiosis morbis et Curatione, Libri iii. (1546)
69. King, A. M. Q., Underwood, B. O., McCahon, D., Newman, J. W. I. and Brown, F. Nature, 293, 479–480 (1981).
70. Cooper, P. D. et al. Intervirology 10, 165–180 (1978).
71. Wild, T. F., Burroughs, J. N. and Brown, F., J. Gen. Virol. 4, 313–320 (1969).
72. Laporte, J., Grosclaude, J., Wantyghem, J., and Rouze, P., C.r. hebd. Acad.Sci.Seanc. Paris, 276, 3399–3401 (1973).
73. Bachrach, H. L., Moore, D. M., McKercher, P. D. and Polatnick, J., J.Immun. 115, 1636–1641 (1975).
74. Kaaden, O. R., Adam, K-H, and Strohmaier, K., J.Gen. Virol. 34, 397–400 (1977).
75. Melven, R. H., Rowlands, D. J. and Brown, F., J.Gen. Virol. 45, 761–763 (1979).
76. Boothroyd, J. C. et al. Nature 290, 800–802 (1981).
77. Boothroyd, J. C., Harris, T. J. R., Rowlands, D. J. and Lowe, P. A. Gene (in press).
78. Kurz, C., Forss, S., Kupper, H., Strohmaier, K. and Schaller, H., Nucleic Acids Res. 9, 1919–1931 (1981).
79. Strohmaier, K., Franze, R. and Adam, K-H. Proc. 5th Int. Congress Virology, Strasbourg (1981).
80. Houghten, R. A., Chang, W. C. and Li, C. H., Int.J. Pept.Prot.Res. 16, 311–320 (1980).
81. Houghten, R. A. and Li, C. H., Anal.Biochem. 98, 36–46 (1979).

Lerner, et al. have been working on FMDV for a long period of time and, for a period, considered that they had identified the optimum specific antigenic determinant peptide fragment for FMDV, only to find that the supposed antigenically active portion did not induce the production of antibodies to FMDV, or induced antibody production at such a low level as to be of little or no value. We were aware that Strohmaier, et al. (unpublished work) had drawn some inferences as to antigenically active portions of their $VP_{th}$ FMDV serotype O gene, and that Kleid, et al. had determined the nucleotide sequence of the $VP_3$ FMDV sterotype A gene (*Science* 214:1125) and that Brown, et al at Pirbright (unpublished) had determined the nucleotide sequence of another serotype A FMDV gene. It was, of course, impossible to determine from the nucleotide sequences which peptide fragment or fragments would be antigenic and, in particular, it was impossible to predict, or even make a guess, as to which peptide fragments would have optimum antigenicity for FMDV virus.

A number of peptides were synthesized, attached to carriers, e.g. KLH, and the resulting antigens were injected into animals. Antibodies from the animals were then challenged with FMDV to determine if the antigen was antigenically efficacious in inducing antibodies to the infectious organism.

It was a totally unexpected discovery that such a comparatively small peptide fragment in the region of 130–160, e.g. about 20 peptides, such sequence 141–160, was extremely antigenic. It is, of course, impossible to determine whether or not there may be other and possibly even more antigenic nucleotide sequences in the FMDV gene, although there is no reason to predict that such would exist. The 130-160 sequence according to this discovery, quite unpredictably and quite surprisingly, seems to be the optimum and probably the ultimate, give or take one or two (perhaps three) amino acids. FMDV mono-specific synthetic antigenic determinant peptide.

It is not presently known how much one can deviate from the exact peptide without losing the highly unexpected activity and efficacy of the vaccine or antigen of which the determinant is the FMDV mono-specific synthetic antigenic determinant; however, it is known from experience that (1) the peptide can be lengthened by a few amino acid units, (2) that at least one or two, perhaps up to four or five substitutions can be made, and (3) that the peptide sequence can be shortened slightly, probably by two or three, perhaps four, without losing the uniqueness of the invention. Such nonsubstantial deviations are known, in principle, to be possible without departing from the concept which has been described and the discovery which has been made and, thus, such minor variations would be regarded by the art as mere equivalent variants of the invention.

Our results show clearly that a single innoculation of the synthetic peptide having about twenty amino acids in the 130–160 region, e.g. region 141–160, elicits sufficient virus neutralizing antibody to protect against challenge with the virus. The protection afforded by the peptide is several orders of magnitude greater than the best results obtained by immunization with the capsid protein $VP_1$, irrespective of whether this is produced by disruption of virus particles or by expression in *E. Coli* cells. Indeed, a small free peptide, it is postulated, may be able to adopt a conformation approximating that it takes up in the virus particle, a situation not likely when it is constrained by the neighbouring amino acids in an improperly folded $VP_1$. An alternative explanation is that immunodominant regions of $VP_1$ may be buried in the virus and irrelevant for neutralization. One clear advantage of the synthetic peptide is its activity in eliciting a protective antibody response by a single innoculation. This good response to a single innoculation is very important because successful immunization against foot-and-mouth disease in the field depends on the vaccines being sufficiently active to produce a protective response with one innoculation. Indeed preliminary work in cattle and pigs shows that the synthetic peptide can elicit an antibody response sufficient to protect these species against the disease.

INDUSTRIAL APPLICATION

The diagnostic and therapeutic applications of the antigens of this invention, and the vaccine and antibody preparations thereof are of great industrial and economic value. Animals, principally swine and cattle, can be protected against the ravages of foot and mouth disease thus increasing the supply of food and, importantly, of protein for the human population.

What is claimed is:

1. An antigen comprising a foot-and-mouth disease virus mono-specific synthetic antigenic determinant peptide having about twenty amino acids corresponding to a twenty amino acid sequence of the foot-and-mouth disease virus protein $VP_1$ in the 130 to 160 region.

2. The antigen of claim 1, wherein the synthetic peptide corresponds substantially to the 141 to 160 sequence region of said $VP_1$ protein.

3. The antigen of claim 2, wherein the synthetic peptide

TYR ASN GLY GLU CYS ARG TYR ASN ARG ASN ALA VAL PRO ASN LEU ARG GLY ASP LEU GLN VAL LEU ALA GLN LYS VAL ALA ARG THR LEU PRO, or

TYR ASN GLY THR ASN LYS TYR SER ALA SER GLY SER GLY VAL ARG GLY ASP PHE GLY SER LEU ALA PRO ARG VAL ALA ARG GLN LEU PRO ALA.

4. The antigen of claim 1, 2 or 3 wherein the foot-and-mouth disease virus mono-specific synthetic antigenic determinant peptide is attached to an antigenic carrier.

* * * * *

UNITED STATES PATENT AND TRADEMARK OFFICE
CERTIFICATE OF CORRECTION

PATENT NO. : 4,544,500

DATED : October 1, 1985

INVENTOR(S) : James L. Bittle and Richard A. Lerner

It is certified that error appears in the above-identified patent and that said Letters Patent is hereby corrected as shown below:

Column 7, line 45, change the title "TABLE 3" to --TABLE 2--.

Claim 3, line 1, change "claim 2" to --claim 1--.

Claim 3, line 2, after "[pep]tide" insert --is--.

Signed and Sealed this

Thirteenth Day of September, 1988

Attest:

DONALD J. QUIGG

*Attesting Officer*  *Commissioner of Patents and Trademarks*